US006207185B1

(12) United States Patent
See et al.

(10) Patent No.: US 6,207,185 B1
(45) Date of Patent: *Mar. 27, 2001

(54) METHOD FOR INDUCING A SYSTEMIC IMMUNE RESPONSE TO AN HIV ANTIGEN

(75) Inventors: Jackie R. See, Reno, NV (US); Darryl M. See, Laguna Niguel, CA (US)

(73) Assignee: Bio-Sphere Technology, Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/948,568

(22) Filed: Oct. 10, 1997

Related U.S. Application Data

(63) Continuation-in-part of application No. 08/882,968, filed on Jun. 26, 1997, now abandoned, which is a continuation of application No. PCT/US97/04634, filed on Mar. 24, 1997, and a continuation of application No. 08/621,802, filed on Mar. 22, 1996, now abandoned, application No. 09/948,568, filed on Oct. 10, 1997, which is a continuation-in-part of application No. 08/920,374, filed on Aug. 29, 1997, and a continuation-in-part of application No. 06/015,576, which is a continuation of application No. PCT/US97/04634, filed on Mar. 24, 1997, and a continuation of application No. 08/621, 802, filed on Mar. 22, 1996, now abandoned.

(51) Int. Cl.[7] .............................. A61K 9/127; A61K 9/133
(52) U.S. Cl. .................. 424/450; 424/184.1; 424/188.1; 424/193.1; 424/196.11; 424/204.1; 424/207.1; 436/829
(58) Field of Search ................................ 424/450, 184.1, 424/188.1, 193.1, 196.11, 204.1, 207.1; 436/829

(56) References Cited

U.S. PATENT DOCUMENTS

| 3,993,754 | 11/1976 | Rahman et al. | 424/177 |
|---|---|---|---|
| 4,117,113 | 9/1978 | Allison et al. | 424/89 |
| 4,145,410 | 3/1979 | Sears | 424/19 |
| 4,199,565 | 4/1980 | Fullerton | 424/89 |
| 4,229,360 | 10/1980 | Schneider et al. | 260/403 |
| 4,235,871 | 11/1980 | Papahadjopoulos et al. | 424/19 |
| 4,235,877 | 11/1980 | Fullerton | 424/89 |
| 4,474,773 | 10/1984 | Shinitzky et al. | 424/199 |
| 4,522,803 | 6/1985 | Lenk et al. | 424/1.1 |
| 4,533,254 | 8/1985 | Cook et al. | 366/176 |

(List continued on next page.)

FOREIGN PATENT DOCUMENTS

| 0217419 | 4/1987 | (EP) . |
| 0333523 | 7/1996 | (EP) . |
| 95/03035 | 2/1995 | (WO) . |

OTHER PUBLICATIONS

Jack Newman, "How Breast Milk Protects Newborns", Scientific American, 1995.

Microfluidics Corp., "The Dermasome Difference is More Than Skin Deep".

J.A.E. Balazsovits, et al., "Analysis of the effect of liposome encapsulation on the vesicant properties, acute and cardiac toxicities, and antitumor efficacy of doxorubicin", Cancer Chemother. Pharmacol. 23:81–86 (1989).

(List continued on next page.)

Primary Examiner—Gollamudi S. Kishora
(74) Attorney, Agent, or Firm—Christie, Parker & Hale, LLP

(57) ABSTRACT

A method is provided for inducing a systemic immune response to an antigen selected from inactivated HIV I and HIV II antigens in a mammal. The method comprises orally administering lyophilized multilaminar liposomes containing the antigen. The liposomes have a size of from 20 nm to 20 microns. The antigen-containing liposomes are absorbed in the Peyer's patches of the gut. Sufficient antigen-containing liposomes are taken up by macrophages in the Peyer's patches to induce a systemic immune response to the antigen.

51 Claims, 9 Drawing Sheets

U.S. PATENT DOCUMENTS

| | | | |
|---|---|---|---|
| 4,588,578 | 5/1986 | Fontain et al. | 424/1.1 |
| 4,708,861 | 11/1987 | Popescu et al. | 424/1.1 |
| 4,749,585 | 6/1988 | Greco et al. | 427/2 |
| 4,776,991 | 10/1988 | Farmer et al. | 264/4.3 |
| 4,820,732 | 4/1989 | Shell et al. | 514/573 |
| 4,880,635 | 11/1989 | Janoff et al. | 424/450 |
| 4,880,835 | 11/1989 | Park et al. | 514/570 |
| 4,955,878 | 9/1990 | See et al. | 604/181 |
| 4,975,282 | 12/1990 | Cullis et al. | 424/450 |
| 4,997,926 | 5/1991 | Haertle et al. | 536/26 |
| 5,008,050 | 4/1991 | Cullis et al. | 264/4.3 |
| 5,030,453 | 7/1991 | Lenk et al. | 424/450 |
| 5,149,529 * | 9/1992 | Ho | 424/88 |
| 5,154,930 | 10/1992 | Popescu et al. | 424/489 |
| 5,208,036 | 5/1993 | Eppstein et al. | 424/450 |
| 5,352,448 * | 10/1994 | Bowersock | 424/438 |
| 5,382,435 * | 1/1995 | Geary | 424/489 |
| 5,573,779 * | 11/1996 | Sato | 424/450 |
| 5,578,309 | 11/1996 | Cutler et al. | 424/274.1 |
| 5,709,879 * | 1/1998 | Barchfeld | 424/450 |
| 5,762,904 | 6/1998 | Okada et al. | 424/1.21 |
| 5,773,027 | 6/1998 | Bergeron et al. | 424/450 |

OTHER PUBLICATIONS

J.W. Cowens, et al., "Initial Clinical (Phase I) Trial of TLC D–99 (Doxorubicin Encapsulated in Liposomes)", Cancer Res. 53:2796–2802 (1993).

N.K. Childers, et al., Oral immunization of humans with dehydrated liposomes containing Streptococcus mutans glucosyltransferase induces salivary immunoglobulin $A_2$, antibody responses, Oral Microbiology & Immunology, pp. 146–153 (1994).

Microfluidics Corp., Laboratory Microfluidizer M–110 Series.

Lewis F. Fries, et al., "Liposomal malaria vaccine in humans: A safe and potent adjuvant strategy", Proc. Natl. Acad. Sci. USA 89:358–362 (1992).

See et al., "Efficacy of a Polyvalent Inactivated–virus Vaccine in Protecting Mice from Infection with Clinical Strains of Group B Coxsackieviruses", Scand J. Infect. Dis. 26:739–747 (1994).

Gregoriadis et al., "The Immunoadjuvant Action of Liposomes: Nature of Immune Response and Influence of Liposomal Characteristics"; Liposomes as Drug Carriers; Chapter 21, pp. 279–307; John Wiley and Sons, Ltd., 1988.

Charles O. Elson, et al., "Oral–Antigen Delivery by way of a Multiple Emulsion System Enhances Oral Tolerance", Annals N.Y. Acad. Sci., No date, pp. 156–162.

D.H. Jones et al., "Orally Administered Microencapsulated *Bordetella pertussis* Fimbriae Protect Mice from *B. Pertussis* Respiratory Infection", Infect. & Immun., Feb., 1996, pp. 489–494.

Smadar Cohen, et al., "Novel Liposome–Based Formulations for Prolonged Delivery of Proteins and Vaccines", J. Liposome Res. 5(4):813–827 (1995).

Steven M. Sugarman, et al., "Liposomes in the treatment of malignancy: a clinical perspective", Critical Reviews in Oncology/Hematology, 12:231–242 (1992).

Gregory Gregoriadis, Ph.D, "The Carrier Potential Of Liposomes in Biology and Medicine (First of Two Parts)", The New England Journal of Medicine, Sep. 23, 1976, 704–710.

Carl R. Alving, "Liposomes as carriers of antigens and adjuvants", J. Immunological Methods, 140 (1991):1–13.

Christine E. Swenson, et al., "Preparation and Use of Liposomes In The Treatment of Microbial Infections", Critical Reviews in Microbiology 15 (Supp. 1) S1–S31 (1988).

Joep J. Bergers, et al., Pharmacy World & Science, 17(1):1–11 (1995).

James Swarbrick, et al., "Liposomes as Pharmaceutical Dosage Forms to Microencapsulation," Encyclopedia of Pharmaceutical Technology, vol. 9, No Date, 1–39.

John H. Eldrige, et al., "Controlled Vaccine Release in the Gut–Associated Lymphoid Tissues, Orally Administered Biodegradable Microspheres Target the Peyer's Patches", Journal of Contolled Release, 11:205–214 (1990).

Darryl M. See, et al., "Successful Immunization of Mice Using Liposomes Containing Inactivated, Prototype Strains of All Six Types of Coxsackievirus Group B. Virus", Vaccine Research, vol. 6, pp. 27–32, 1997.

Sophie Kerneis, et al., "Conversion by Peyer's Patch Lymphocytes of Human Enterocytes into M Cells that Transport Bacteria", Science, vol. 227, August 15, 1997.

James L. Madara, "The Chameleon Within: Improving Antigen Delivery", Science, vol. 227, Aug. 15, 1997.

Aramaki Pharm. Res. 10 #8 p. 1228, 1993.*

Gregoriadis in Liposomes as Drug carriers 1988 p. 279.*

Aramaki, Y. et al., "Stability of lipsomes in vitro and their uptake by rat Peyer's patches following oral administration.", Pharm Res 1993 Aug; 10(8):1228–1231 (Abstract).

Bowersock, T.L. et al., "Induction of pulmonary immunity in cattle by oral administration of ovalbumin in alginate microspheres.", Immunol Lett 1998 Jan; 60(1):37–43 (Abstract).

Chen, H. et al., "Lectin–bearing polymerized Lipsomes as potential oral vaccine carriess.", Pharm Res 1996 Sep;13(9):1378–1383 (Abstract).

Choi, M.J. et al., "pH–sensitive Lipsomes containing polymerized phosphatidylethanolamine and fatty acid.", J Biochem (Tokyo) 1992 Nov;112(5):694–699 (Abstract).

Eldridge, J.H. et al., "Biodegradable microspheres as a vaccine delivery system.", Mol Immunol 1991 Mar;28(3):287–294 (Abstract).

Freeman. F.J. et al., "Permeability studies on lipsomes formed from polymerizable diacetylenic phospholipids and their potential applications as drug delivery systems." Biochim Biophys Acta 1987 May 19;924(2):341–351 (Abstract).

Heller, J. et al., "Controlled release of water–soluble macromolecules from bioerodible hydrogels.", Biomaterials 1983 Oct;4(4):262–266 (Abstract).

O'Connor, C.J. et al., "Bile salt damage of egg phosphatidylcholine lipsomes.", Biochim Biophys Acta 1985 Jul. 11:817(1):95–102 (Abstract).

O'Hagan, D.T. et al., "Biodegradable Microparticles for oral immunization.", Vaccine 1993;11(2):149–154 (Abstract).

O'Hagan, D.T. et al., "Biodegradable Microparticles as Oral Vaccines", Advances in Mucosal Immunology, Ed. by J. Mestecky et al, Plenum Press, New York, 1995, 1463–1467.

Okada, J., et al., "In virto evaluation of polymerized liposomes as an oral drug delivery system.", Pharm Res 1995 Apr;12(4):576–582 (Abstract).

Otterlei, M. et al., "Induction of cytokine production from human monocytes stimulated with alginate.", J Immunother 1991 Aug; 10(4):286–291 (Abstract).

Regen, S.L., "Polymerized phosphatidylcholine vesicles as drug carriers.", Ann N Y Acad Sci 1985; 446;296–307 (Abstract).

Weng, C.N. et al., "Protective effects of an oral microencapsulated Mycoplasma hyopneumoniae vaccine against experimental infection in pigs.", Res Vet Sci 1992 Jul;53(1):42–46 (Abstract).

* cited by examiner

METHOD FOR INDUCING A SYSTEMIC IMMUNE RESPONSE TO AN HIV ANTIGEN

CROSS REFERENCE TO RELATED APPLICATIONS

This application is a continuation-in-part of U.S. application Ser. No. 08/882,968, filed Jun. 26, 1997, which is a continuation-in-part of International applicatin No. PCT/US97/04634, filed Mar. 24, 1997, which is a continuation of U.S. application Ser. No. 08/621,802, filed Mar. 22, 1996, now abandoned; this application is also a continuation-in-part of U.S. application Ser. No. 08/920,374, filed Aug. 29, 1997, which is a continuation of International application No. PCT/US97/04634, filed Mar. 24, 1997, which is a continuation-in-part of U.S. application Ser. No. 08/621,802, filed Mar. 22, 1996, now abandoned.

FIELD OF THE INVENTION

This invention relates to a method for inducing a systemic immune response to an HIV antigen and more particularly to vaccines suitable for oral administration.

BACKGROUND OF THE INVENTION

The epithelial surfaces of the body serve as a barrier to antigenic material. However, those surfaces are by no means impenetrable. The mucosal immune system provides the next major line of defense against a majority of human pathogens. The mucosal immune system includes gut-associated lymphoid tissue (GALT), bronchus-associated lymphoid tissue, the salivary glands, the conjunctiva, the mammary gland, parts of the urogenital tract, and the middle ear.

GALT consists of two types of lymphoid aggregates. The first is referred to as Peyer's patches and the second consists of isolated lymphoid follicles. Peyer's patches have a defined micro-structure including a central B cell dependent follicle and T cell dependent regions adjacent to the follicle. The lymphocytes in Peyer's patches are heterogeneous, including B cells which express IgM, IgG, IgA, and IgE and various regulatory and cytotoxic T cells. Peyer's patches also contain specialized macrophages. The Peyer's patches are covered by M cells, which are specialized lympho-epithelium cells.

In GALT, ingested antigens produce a local immune response. The antigens are taken up by the M cells, which deliver the antigen to the underlying lymphocytes in the tissue. This results in the production of IgA at various secretory effector sites following the migration of activated lymphocytes through the efferent, lymphatic and circulatory system.

The absorption of antigens by the Peyer's patches can induce a systemic immune response if the antigen is taken up by macrophages in the Peyer's patches. Macrophages induce a systemic response by processing antigens and presenting them to lymphocytes. The lymphocytes then become activated and cause the production of systemic antibodies specific to the antigens.

Childers et al. (Oral Microbiol. Immunol. 1994:9:146–153) reported that lyophilized liposomes containing *S. mutans* antigen can be administered orally to human patients and will be absorbed by GALT to elicit a local immune response. No systemic response was observed however.

Traditionally, to obtain a systemic immune response by oral administration of an antigen, it was required that the antigen be associated with an adjuvant. The presence of the adjuvant permits the antigen/adjuvant combination to be recognized by the CD4 cells, which send signals to B cells to produce antibodies, and by the cytotoxic lymphocytes, which kill the infecting organism in affected host cells. Without the presence of the adjuvant, the CD4 cells and cytotoxic lymphocytes ignore the free antigen.

Typical adjuvants include alum, Freund's adjuvant, incomplete Freund's adjuvant and indotoxin. These adjuvants typically induce an inflammatory response. Other typical adjuvants are immuno stimulating complexes (iscoms) that contain Quil A. These adjuvants typically cause clumping of antigens.

A need therefore exists to induce a systemic immune response by oral administration without the presence of an adjuvant and without inducing the above-described adjuvant effects, but instead by uptake by the macrophages in the Peyer's patches.

SUMMARY OF THE INVENTION

The present invention provides a method for inducing a systemic immune response to one or more antigens in a mammal and does not require the presence of an adjuvant. According to the present invention, the lyophilized antigen-containing liposomes do not directly target the CD4 cells and cytotoxic lymphocytes, but instead are taken up by the macrophages in the Peyer's patches. The macrophages express the antigen in conjunction with self major histocompatibility antigen I and II (SMH I and SMH II). The CD4 cells recognize the antigen expressed with SMH I, and the cytotoxic lymphocytes recognize the antigen expressed with SMH II. Accordingly, the present methods involve an intermediate step, being taken up by the macrophages, which is different from the process that occurs when an antigen/adjuvant combination is orally administered. Thus, the present invention involves a method whereby the antigen containing liposomes can be orally administered without an adjuvant to induce a systemic immune response. Moreover, the inventive methods do not generate an adjuvant effect, e.g., an inflammatory response or clumping of antigens.

The inventive method comprises first incorporating at least one antigen selected from inactivated HIV I and HIV II antigens into liposomes, preferably multilamellar liposomes having a size from about 20 nm to about 20 microns or greater, preferably from about 200 nm to about 10 microns and more preferably from about 1 micron to about 5 microns. The antigen-containing liposomes are then lyophilized and packaged in a suitable form, such as a pill or capsule, for oral ingestion. Means, such as an enteric coating are provided for preventing breakdown of the preparation in the stomach but allowing digestion in the gut, i.e., small intestine. Once orally ingested, the preparation passes through the stomach into the gut wherein antigen-containing liposomes are absorbed in the Peyer's patches of the gut. In the Peyer's patches, sufficient antigen-containing liposomes are taken up by macrophages to induce a systemic immune response and preferably a long-term systemic immune response to the antigen(s).

The invention further provides a preparation suitable for oral ingestion for inducing a systemic response, and preferably a long-term systemic immune response, to one or more antigens selected from inactivated HIV I and HIV II antigens. The composition comprises lyophilized, preferably multilamellar, liposomes that contain the antigen(s). The liposomes have a size, before lyophilization, of from about 20 nm to about 20 microns or greater, preferably from about 200 nm to about 10 microns, and more preferably from about one to about five microns. A particularly preferred composition comprises liposomes of varying sizes including small liposomes, i.e., about 20 mn to about 1 micron, medium liposomes, i.e., about 1 to about 3 microns, and large liposomes, i.e. about 3 to about 20 microns or greater and preferably about 3 to about 5 microns. It is presently preferred that such a composition comprise at least 5% by volume small liposomes, at least 10% by volume medium liposomes, and at least 20% by volume large liposomes. The composition preferably comprises means for preventing breakdown of the preparation in the stomach but for allowing digestion of the liposomes in the gut. In the gut, the liposomes are absorbed by Peyer's patches and sufficient liposomes are taken up by macrophages to stimulate a long term systemic immune response.

DETAILED DESCRIPTION

Figure 1:
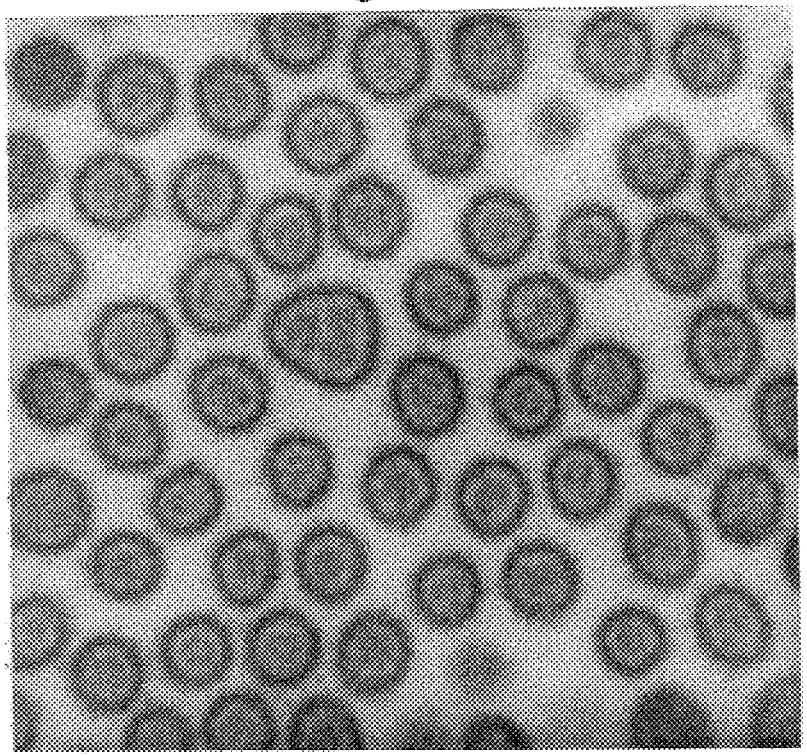
FIG. 1 is an electron photomicrograph (magnification: 100,000×) of liposomes in lymphoid tissue of a Peyer's patch.
Figure 2:
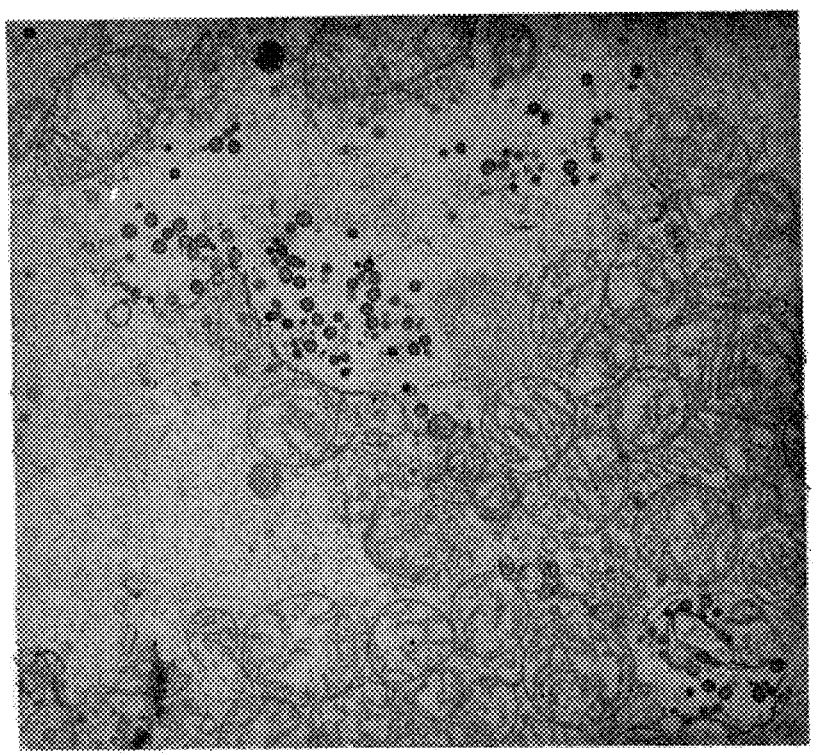
FIG. 2 is an electron photomicrograph (magnification: 10,000×) of lymphoid tissue within the Peyer's patch.

Some antigens require intracellular processing by antigen processing cells, such as macrophages or Kupffer cells before being presented to T lymphocytes as a processed antigen. This processed antigen is then displayed on the macrophage surface in association with HLA molecules and presented to the T cell to confer systemic immunity. The macrophage also produces certain soluble cytokines that have an important role in T-cell activation, which confers systemic immunity as well.

Therefore, it is critical that the presenting antigen, such as liposomal lyophilized antigen, enter the macrophage of the GALT for processing to confer systemic immunity, and this is dependent upon the size of the liposome presented to the GALT.

Size and composition of the liposomes are important in determining the duration of the systemic immune response to the incoiporated antigen. Administration of liposomes of varying size and composition ensure a long lasting immune response, and thus avoid the need for repeated vaccine administrations. Since the half life of the macrophage is approximately 90 days, the presentation of an antigen taken up by GALT macrophages can last up to 180 days for conferring systemic immunity.

It has been found that liposomes containing one or more antigens and having a particular size from about 20 nm to about 20 microns or greater, preferably from about 200 nm to about 10 microns and more preferably from about 1 to about 5 microns, when administered orally to a mammal in lyophilized form, will be absorbed in the Peyer's patches of the gut and taken up by macrophages in the Peyer's patches. The presence of liposomal antigen in the Peyer's patches (outside of the macrophages) initiates a local immune response to the antigen as the liposomes breakdown and release the antigen. The uptake of sufficient liposomal antigen in the macrophages stimulates a systemic immune response, and preferably a long-term systemic immune response, to the antigen(s) as the liposomes breakdown within the macrophages to release antigen.

As used herein, "local immune response" refers to mucosal IgA, which confers protection from organisms in the bowel lumen and is characterized by secretion of local sIgA.

As used herein, "systemic immune response" refers to whole body production and circulation of organism specific humoral and cellular immune cells and is characterized by organism specific immune globulin (antibodies) and cytotoxic mononuclear cells.

As used herein, "long term systemic immune response" means a detectible systemic immune response to an antigen that lasts at least 150 days after administration of the antigen.

As used herein, "sufficient liposomal antigen to stimulate a systemic immune (or long-term systemic immune) response" means that amount of antigen-containing liposomes that affect a detectible systemic immune response (or long-term systemic immune response). A systemic immune response may be confirmed by neutralizing antibody testing or other means of specific antibody testing, cytotoxic mononuclear cell assays and in vivo microbe challenge experiments, as is well known in the art.

As used herein, "antigens" may be any substance that, when introduced into a mammal, will induce a detectable immune response, both humoral and cellular. As used herein, the term "antigen" also includes any portion of an antigen, e.g., the epitope, which can induce an immune response. In a particularly preferred embodiment of the invention, the antigen is an attenuated or killed microorganism, such as a virus or bacteria, rendering the preparation an oral vaccine against that microorganism.

As used herein, "inactivated HIV I and HIV II antigens" include any substance that, when introduced into a mammal, will induce a detectable immune response, both humoral and cellular. Typical HIV I and HIV II antigens include but are not limited to, p24 antigen, gp120, gp41, and envelope proteins.

The liposomes of the present invention may be made of any suitable phospholipid, glycolipid, derived lipid, and the like. Examples of suitable phospholipids include phosphatide choline, phosphatidyl serine, phosphatidic acid, phosphatidyl glycerin, phosphatidyl ethanolamine, phosphatidyl inositol, sphingomyelin, dicetyl phosphate, lyso-phosphatidyl choline and mixtures thereof, such as soybean phospholipids, and egg yolk phospholipids. Suitable glycolipids include cerebroside, sulphur-containing lipids, ganglioside and the like. Suitable derived lipids include cholic acid, deoxycholic acid, and the like. The presently preferred lipid for forming the liposomes is egg phosphatidylcholine.

The liposomes may be formed by any of the known methods for forming liposomes and may be loaded with antigen according to known procedures. Known methods for forming liposomal antigen are described, for example, in U.S. Pat. No. 4,235,871 to Papahadjopoulos, et al., and Oral Microbiology and Immunology, 1994, 9:146–153, the disclosures of which are incorporated herein by reference. What is formed is an emulsion comprising liposomal antigen.

Viral, bacterial and parasitic antigens may all be incorporated into liposomes and generate long-term immunity. In all cases, varying the size of the liposome for each antigen is crucial. The antigens may first be individually incorporated into liposomes and then given individually or mixed with liposomes containing other antigens. Viral, bacterial and/or parasitic antigens may be combined. In an exemplary embodiment of the invention, the liposomes are loaded with p24 antigens. The liposomes may also be loaded with other HIV antigens or whole virus.

It is also understood that rather than loading multiple viral antigens into each liposome, preparations may be prepared comprising a mixture of liposomes wherein each liposome contains only a single antigen. If desired, the liposomes may be loaded with a therapeutic drug in addition to the antigen.

It is preferred that the liposomes used in the present invention have an average mean diameter from about 20 nm to about 20 microns, preferably from about 200 nm to about 10 microns, and more preferably of from about 1 micron to about 5 microns.

Liposomes larger than about 20 microns are generally not preferred because they tend not to be taken up by the macrophages and only affect a local secretory antibody response. That is, the presence of large antigen-containing liposomes in the lymphoid tissue of the Peyer's patches will induce gut-associated lymphoid tissue (GALT) to produce IgA antibodies to destroy the antigen. However, no systemic immune response is induced.

Liposomes smaller than about 20 nm are generally not preferred because they also tend not to be processed adequately by macrophages. These smaller liposomes tend to reside in the lymphoid tissue until they eventually are absorbed into the bloodstream and are destroyed by the reticuloendothelial (RE) system. The smaller liposomes may induce a low grade production of secretory IgA, but do not stimulate systemic immunity.

It has been found that antigen-containing liposomes of from about 20 nm to about 20 microns, preferably from about 200 nm to about 10 microns and more preferably from about 1 micron to 5 microns tend to be absorbed by macrophages in the Peyer's patches. The macrophages digest the liposomes to release the antigen, which is then presented or displayed at the surface of the macrophage. The macrophages act as antigen-presenting cells which process and present the antigen to systemic lymphocytes thereby inducing a systemic immune response to the antigen. The macrophages display the antigen in conjunction with the major histocompatibility complex II (MHC II) glycoproteins to T-helper cells. T-helper cells activate B cells, which proliferate and differentiate into mature plasma cells that secrete copious amounts of immunoglobulins. In the systemic response, the immunoglobulins secreted are initially IgM followed by IgG.

It is preferred that the liposomes be a mixture of sizes. Such heterogeneous sizes of liposomes are preferred as they are broken down over a period of time, e.g., up to 180 days or more by the macrophages. Preferably, the mixture of sizes will include liposomes having a size of about 20 nm to about 1 micron (small liposomes), liposomes having a size of about 1 micron to about 3 microns (medium liposomes) and liposomes having a size of about 3 to about 20 microns (large liposomes). Preferred large liposomes are those having a size of from about 3 to about 5 microns. Preferably, there is at least about 5% by volume of each size of liposomes, i.e., small, medium and large, in the composition. More preferably, there is at least about 5% by volume of small liposomes, at least 10% by volume medium liposomes, and at least 20% by volume large liposomes. A particularly preferred composition comprises about 10% by volume small liposomes, about 25% by volume medium liposomes and about 65% by volume large liposomes.

In a composition containing a heterogeneous population of liposomes, there may be a uniform distribution of sizes or two or more discrete, homogeneous populations. A combination of small, medium and large sizes is preferred because a smoother amnestic antibody curve is generated producing the most effective and dependable long-term immunity.

Compositions comprising liposomes of various sizes allow antigens to be released in the macrophages over a long period of time, thereby continuing to stimulate a systemic immune response over a period of time. The small size liposomes are taken up by the macrophages quickly and provide an immediate systemic immune response. Medium size liposomes are taken up by the macrophages, but at a slower pace. These liposomes act as a booster, i.e., provide an amnestic response. The larger size liposomes take even longer to be taken up by the macrophages and act as a second booster, i.e., provide a second amnestic response. Hence, use of liposomes of varying sizes enables a single dose of the antigen-containing liposomes to be sufficient to result in long term, and even permanent, immunity to the antigen.

The liposomes may be unilamellar or multilamellar. Production of unilamellar and multilamellar liposomes is also well known in the art and is described, for example, in U.S. Pat. No. 5,008,050 to Cullis et al. and U.S. Pat. Nos. 5,030,453 and 9,522,803 both to Lenk, et al., the disclosures of which are incorporated herein by reference.

Preparation of a homogeneous population may be accomplished by conventional techniques such as extrusion through a filter, preferably of 200 nm to 20 micron pore size, the filter being either the straight path or tortuous path type. Other methods of treating liposomes to form a homogenous size distribution are ultrasonic exposure, the French press technique, hydrodynamic shearing, homogenization using, for example, a colloid mill or Gaulin homogenizer, and microfluidization techniques. Microfluidization is one presently preferred method. Other techniques involving sonication are also preferred.

Microfluidization is described, for example, in U.S. Pat. No. 4,533,254 to Cook, et al., which is incorporated herein by reference. In a preferred microfluidization procedure, the liposomal emulsion is forced at high pressure through a small diameter opening and splattered onto a wall and then collected.

In a particularly preferred embodiment of the invention, the liposomes are passed one to ten and preferably 4 times through an M-110 Series Laboratory Microfluidizer manufactured by Microfluidics Corporation at a pressure of, e.g., 14,000 pounds per square inch to achieve a generally homogenous population of liposomes having an average mean diameter of about 1 micron. Liposomes of other sizes can be prepared using the same method by adjusting the number of runs through the microfluidizer, the pressure, and flow rate.

In sonication techniques, the raw materials for the liposomes, e.g., phospholipids, are combined with antigens, placed in a sonicator, and sonicated for a time, at a temperature and at a speed sufficient to obtain liposomes of the desired size. For example, in a particularly preferred method, raw materials are placed in a Brinkman Inc. or Beckman Inc. Sonicator and sonicated at 1,000 to 10,000 meters per second at 50° C. for 20, 5 and 2 minutes to obtain small, medium and large liposomes, respectively. Typically, larger sonication times result in smaller liposomes.

To stabilize the liposomal antigen, the emulsion is lyophilized. Lyophilized liposomal antigen can be stored at room temperature for one half to three years without degradation of the liposomes or antigen.

Lyophilization may be accomplished by any method known in the art. Such procedures are disclosed, for example, in U.S. Pat. No. 4,880,836 to Janoff, et al., the disclosure of which is incorporated herein by reference. Lyophilization procedures preferably include the addition of a drying protectant to the liposome suspension. The drying protectant stabilizes the liposome suspension. The drying protectant stabilizes the liposomes so that the size and content are maintained during the drying procedure and through rehydration. Preferred drying agents are saccharide sugars including dextrose, sucrose, maltose, manose, galactose, raffinose, trehalose lactose, and triose sugars which are preferably added in amounts of about 5% to about 20% and preferably about 10% by weight of the aqueous phase of the liposomal suspension. Dextrose, sucrose and maltose are presently preferred. Manitol may be used in conjunction with any of the saccharides. Additional preservatives such as BHT or EDTA, urea, albumin, dextran or polyvinyl alcohol may also be used.

The lyophilized liposomal antigen may be packaged for oral administration in either a pill form or a capsule. An enteric coating is preferably applied to the liposomal antigen to prevent breakdown in the stomach.

The enteric coating may be made of any suitable composition. Suitable enteric coatings are described, for example, in U.S. Pat. Nos. 4,311,833 to Namikoshi, et al.; 4,377,568 to Chopra; 4,385,078 to Onda, et al.; 4,457,907 to Porter; 4,462,839 to McGinley, et al.; 4,518,433 to McGinley, et al.; 4,556,552 to Porter, et al.; 4,606,909 to Bechgaard, et al.; 4,615,885 to Nakagame, et al.; and 4,670,287 to Tsuji, all of which are incorporated herein by reference.

Preferred enteric coating compositions include alkyl and hydroxyalkyl celluloses and their aliphatic esters, e.g., methylcellulose, ethylcellulose, hydroxyethylcellulose, hydroxypropylcellulose, hydroxybutylcellulose, hydroxyethylethylcellulose, hydroxyprophymethylcellulose, hydroxybutylmethylcellulose, hydroxypropylcellulose phthalate, hydroxypropylmethylcellulose phthalate and hydroxypropylmethylcellulose acetate succinate; carboxyalkylcelluloses and their salts, e.g., carboxymethylethylcellulose; cellulose acetate phthalate; polycarboxymethylene and its salts and derivatives; polyvinylalcohol and its esters, polycarboxymethylene copolymer with sodium formaldehyde carboxylate; acrylic polymers and copolymers, e.g., methacrylic acid-methyl methacrylic acid copolymer and methacrylic acid-methyl acrylate copolymer; edible oils such as peanut oil, palm oil, olive oil and hydrogenated vegetable oils; polyvinylpyrrolidone; polyethyleneglycol and its esters, e.g., and natural products such as shellac.

Other preferred enteric coatings include polyvinylacetate esters, e.g., polyvinyl acetate phthalate; alkyleneglycolether esters of copolymers such as partial ethylene glycol monomethylether ester of ethylacrylate-maleic anhydride copolymer or diethyleneglycol monomethylether ester of methylacrylate-maleic anhydride copolymer, N-butylacrylate-maleic anhydride copolymer, isobutylacrylate-maleic anhydride copolymer or ethylacrylate-maleic anhydride copolymer; and polypeptides resistant to degradation in the gastric environment, e.g., polyarginine and polylysine.

Mixtures of two or more of the above compounds may be used as desired.

The enteric coating material may be mixed with various excipients including plasticizers such as triethyl citrate, acetyl triethyl citrate, diethyl phthalate, dibutyl phthalate, dibutyl sebacate, dibutyl tartrate, dibutyl maleate, dibutyl succinate and diethyl succinate and inert fillers such as chalk or pigments.

The composition and thickness of the enteric coating may be selected to dissolve immediately upon contact with the digestive juice of the intestine. Alternatively, the composition and thickness of the enteric coating may be selected to be a time-release coating which dissolves over a selected period of time, as is well known in the art.

EXAMPLE 1

To establish the effective absorption of lyophilized liposomes by Peyer's patches and uptake by macrophages, the following protocol was followed:

Preparation of antigen-containing liposomes:

Antigen-containing liposomes having a diameter of approximately 142 nanometers used in the experimental study described below were prepared according to the following procedure.

1. 2250 ml of water (double distilled) to beaker (keep cool) and set with a nitrogen sparge for at least 30 minutes.

2. Add 225 gms of maltose (Sigma M5885) to the water and mix until dissolved. Keep the nitrogen sparge going. Mixture at ph of 4.81.

3. In another beaker 10.59 gms of egg phosphatidylcholine (EPC) (Sigma) is combined with 8.38 ml of ethanol (anhydrous, Sigma E3884) and mixed until dissolved. To this add 67.5 mg of BHT and mix until dissolved. To this mixture add 2160 mg of purified Coxsackie B viral antigen and mix until dissolved. Use the remaining 4.19 ml of ethanol to rinse any remaining Coxsackie B antigen in the weighing container into the mixture.

4. Draw the ethanol solution into a 10 ml glass syringe and add to the maltose solution over 11 minutes with continued nitrogen sparge. Keep ph <7.0 (goes into microfluidizer at ph 4.81). Measure. Hand blade mixture. Keep everything cool, e.g. 1.5 degrees C.

5. Microfluidizer. Four (4) passes through the microfluidizer at 110° F.:

| Weight of Materials to be Used | |
|---|---|
| EPC | 10.59 grams |
| Maltose | 225 grams |
| Ethanol | 12.57 ml |
| BHT | 67.5 mg |
| Coxsackie B | 2160 mg |
| (USP) Water | 2250 ml |
| Pressure 16,000 PSI | |

6. Take 2.7 ml of the finished product and lyophilize in approximately 1,000 6 ml Wheaton eye dropper bottles. Lyophilization was accomplished according to the following cycle:

1. Shelfat ≦−45° C. for at least one (1) hour before loading.

2. Load product keep at ≦−45° C. for twelve (12) hours.

3. Vacuum to ~50μ.

4. Shelf temperature at −28° C. to −20° C. for 59 hours.

5. Shelf temperature rose from −20° C. to −5° C. during subsequent ten (10) hours. Visually product needed extra time at −20° C.

6. Shelf reset at −22° C. and maintained at −22° C. to −18° C. for thirty-six (36) hours.

7. Shelf reset +25° C. and held at 25° C. for 48 hours.

It is anticipated that the following lyophilization cycle will provide the same results in a shorter time.

1. Shelf to ≦45 ° C. for at least one (1) hour before loading.

2. Load product, keep at ≦−45° C. for at least six (6) hours.

3. Vacuum to ≦100μ.

4. Shelf to −28° C. for 50 hours.

5. Shelf to +25 ° C. for 40–50 hours.

Experimental:

100 micrograms of lyophilized liposomes 142 nanometers in diameter were suspended in 0.3 ml of 0.5% xanthum gum aqueous solution. The mixture was given via a gavage tube to four week old male CD-1 mice. Five mice were given the liposomal preparation and five mice were given 0.5% xanthum only as controls. For one week the ten mice were kept on ad lib diet and water ad lib. On day seven the mice were anesthetized with methyloxyfluorane and through a mid-line abdominal incision the peritoneum was entered. The small bowel was resected and examined for the Peyer's patches. The Peyer's patches from the small bowel were removed and placed in one molar phosphate buffer minced with a straight razor into less than 1 mm sections on wax paper.

The preparation was then fixed at room temperature with 4% glutaraldehyde in two molar phosphate buffer, washed three times with one molar phosphate buffer and taken to the electronmicroscopy facility. The preparation was then dehydrated and mounted in epoxy resin, cut with a microtome, stained with osmium tetroxide, then examined under a Zeis CR10 electron microscope. The Peyer's patches were then photographed and labeled as noted.

Figure 3:
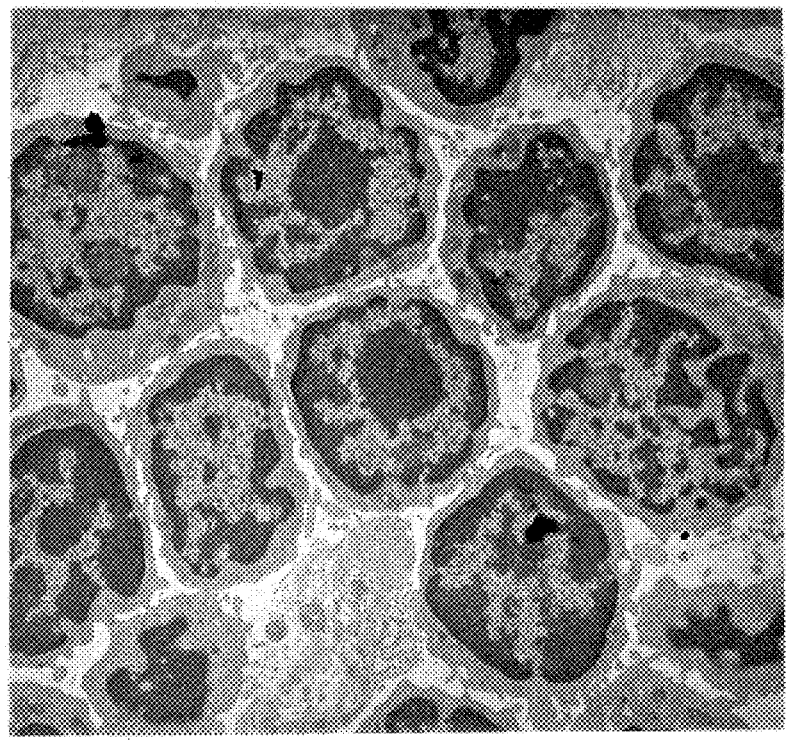
FIG. 3 is an electron photomicrograph (magnification: 20,000×) of splenic lymphoid cells.
Figure 4:
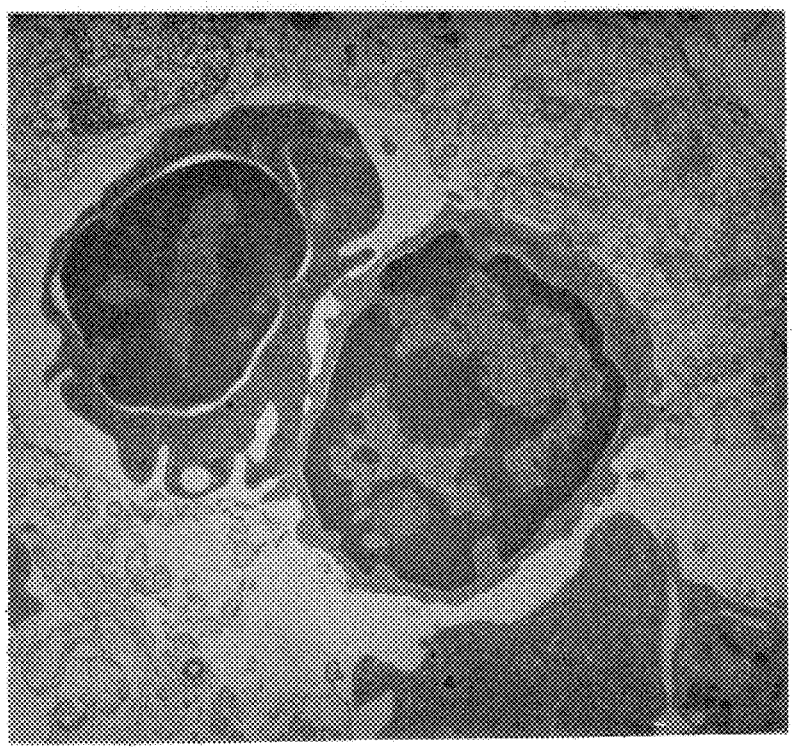
FIG. 4 is an electron photomicrograph (magnification: 60,000×) of splenic lymphoid cells.
Figure 5:
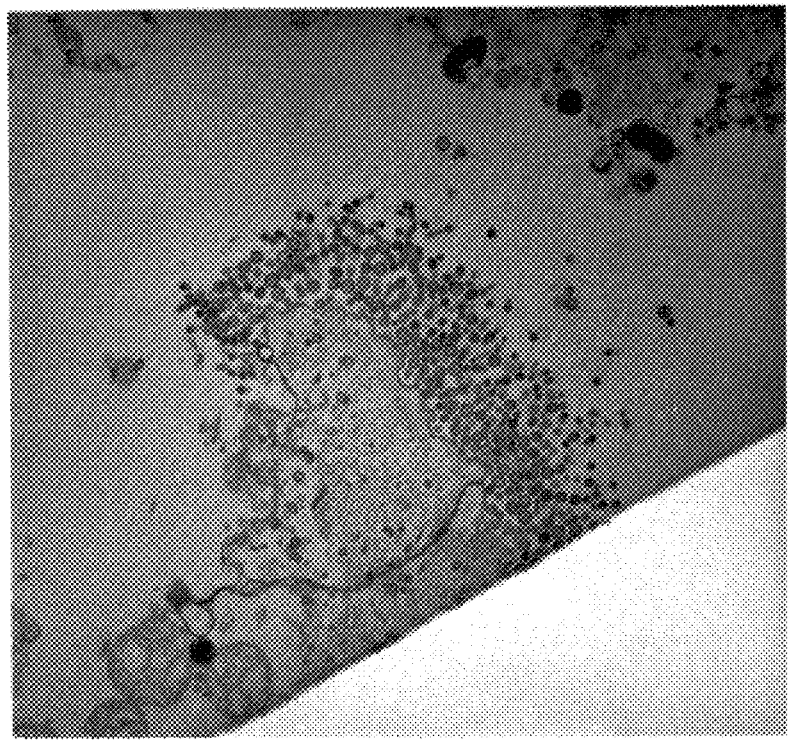
FIG. 5 is an electron photomicrograph (magnification: 15,000×) of a macrophage in the Peyer's patch.
Figure 6:
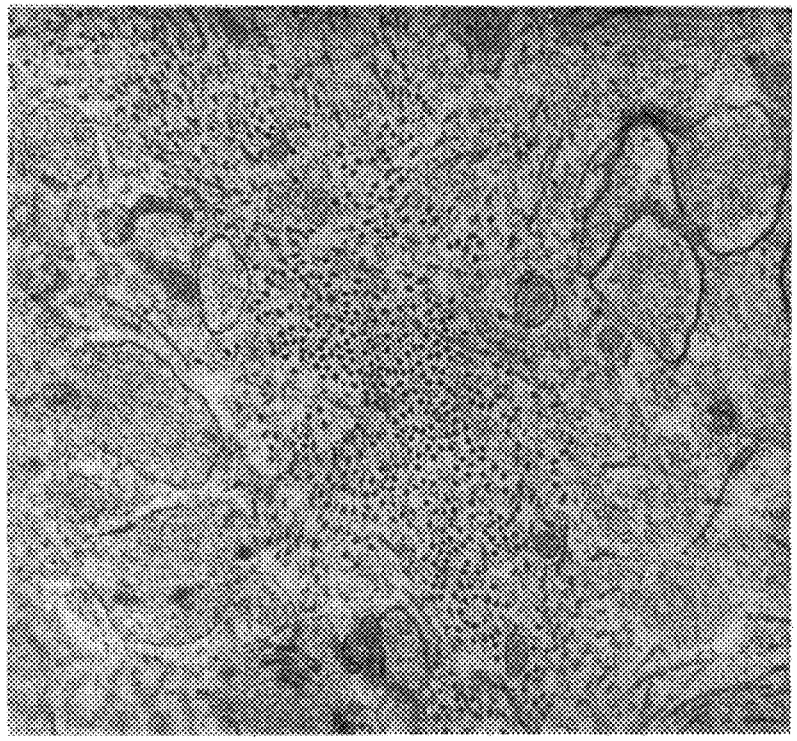
FIG. 6 is an electron photomicrograph (magnification: 10,000×) of an extracellular space in the Peyer's patches.
Figure 7:
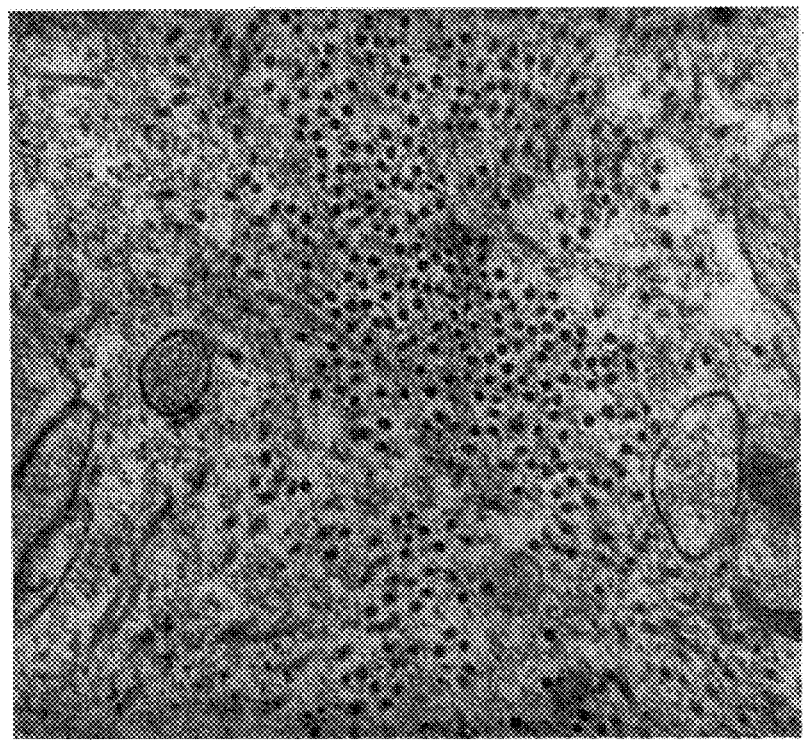
FIG. 7 is an electron photomicrograph (magnification: 15,000×) of an extracellular space in the Peyer's patches.
Figure 8:
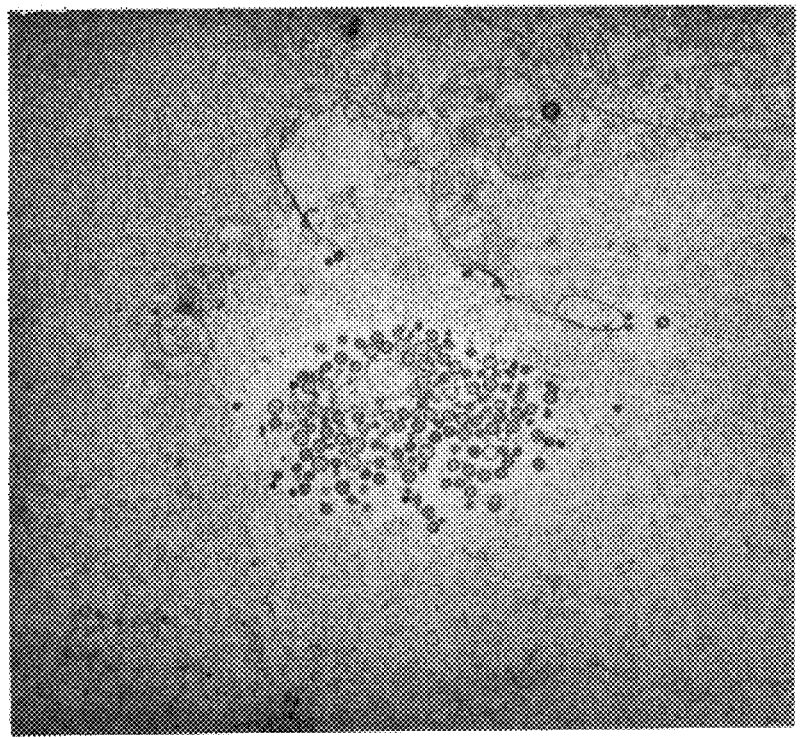
FIG. 8 is an electron photomicrograph (magnification: 10,000×) of liposomes surrounding a white blood cell in a venule of the Peyer's patch.
Figure 9:
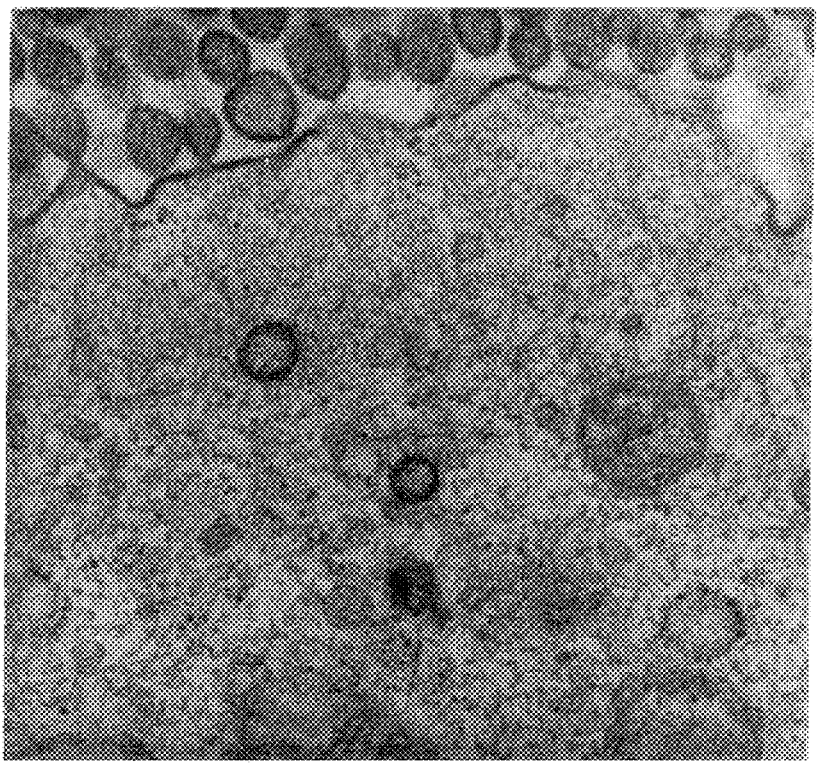
FIG. 9 is an electron photomicrograph (magnification: 50,000×) of the cytoplasm and cellular membrane of a macrophage in the Peyer's patch.
Figure 10:
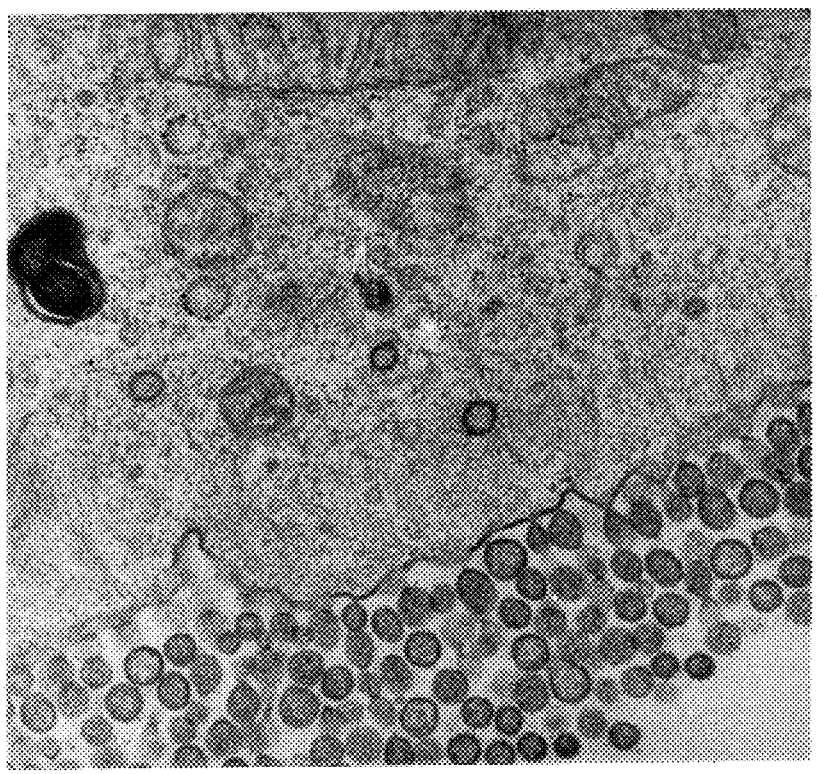
FIG. 10 is an electron photomicrograph (magnification: 40,000×) showing liposomes at the cellular membrane and inside a macrophage in the Peyer's patch.
Figure 11:
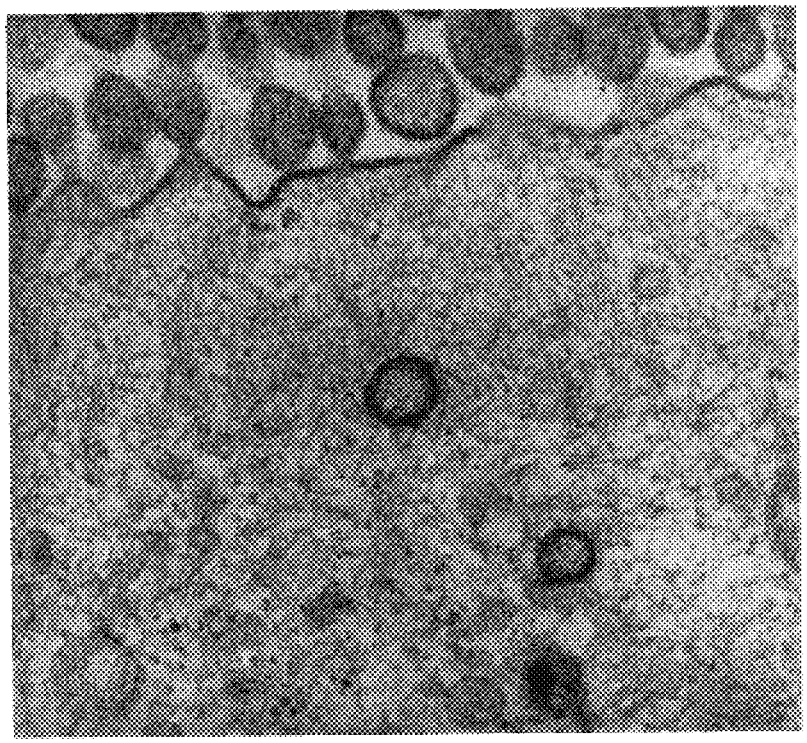
FIG. 11 is an electron photomicrograph (magnification: 70,000×) showing liposomes inside a macrophage in the Peyer's patch.
Figure 12:
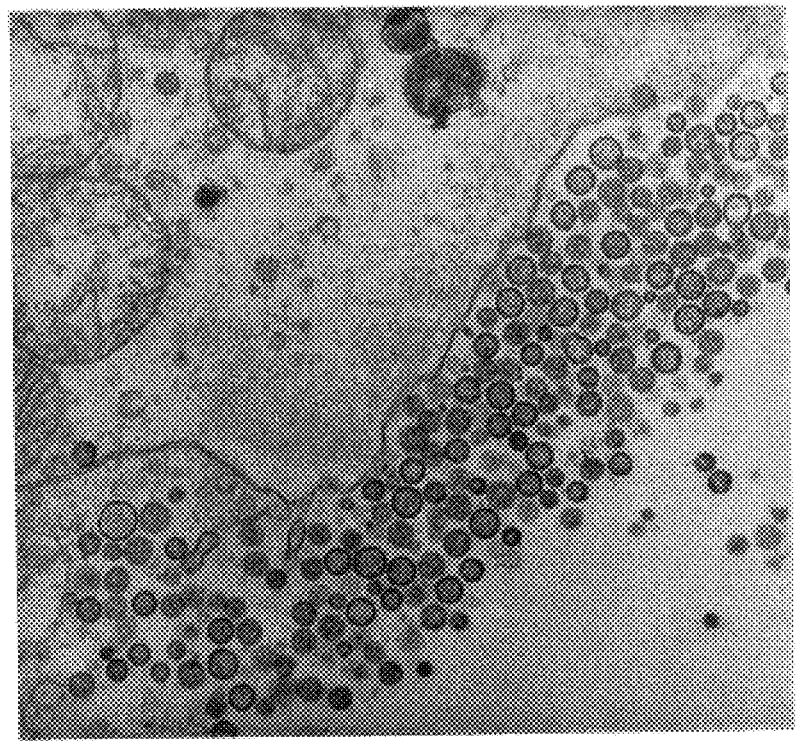
FIG. 12 is an electron photomicrograph (magnification: 75,000×) showing liposomes adhering to a venule wall in the lymphoid cells of the Peyer's patch.

The spleen and Peyer's patches of the gut were sectioned and slides were prepared. Photomicrographs were taken and are presented here as FIGS. 1–12. The photomicrographs show liposomes (FIG. 1) residing in venules and extracellular tissue of the Peyer's patch (FIGS. 2, 6, 7, 8, 12). They also show that the liposomes were not present in the splenic lymphoid tissue which indicate that the liposomes were staying in the Peyer's patches and not circulating through the blood stream in the mouse. (FIGS. 3, 4). Finally, the photomicrographs show liposomes being absorbed and digested by macrophages (FIGS. 5, 9, 10, 11).

EXAMPLE 2

Virus and Cells

Virus stocks of CVB5 strain C59 were prepared in monolayers of monkey kidney (MK) cells using an inoculum giving an MOI of 1 pfu/cell in supplemental Leibovitz's L15 medium as described in See D M Tilles J G., "EFfficacy of a Polyvalent Inactivated-virus Vaccine in Protecting Mice from Infection with Clinical Strains of Group B Coxsackie viruses." Scand. J. Infect. Dis. 26:739–747, 1994, the disclosure of which is incorporated herein by reference. Flasks were observed daily for cytopathic effect (cpe) until cpe reached 4+. At that time, the virus was harvested, aliquoted and frozen at −80° C. until further use.

Animals

Male CD-1 Mice 16–18 g were obtained from Charles Rivers Farms, Wilmington, Mass.

Preparation of Viral Antigen

One strain of coxsackieviruses groups B1–6 were absorbed to monolayers of MK cells at a multiplicity of 1 pfu/cell and incubated as described. When maximal cytopatic effect was observed, the virus-containing media for a single strain was harvested and pooled. Aliquots were stored and tested for viral titer as previously described in See, D. M., Tilles, J. G., "Efficacy of a Polyvalent Inactivated-virus Vaccine in Protecting Mice from Infection with Clinical Strains of Group B Coxsackieviruses." Scand. J. Infect. Dis. 26:739–747, 1994.

Microencapsulation

Viral proteins were encapsulated with 3 different particle size liposomes as follows: Before beginning, 3 round bottom flasks were labeled A (2 minutes), B (5 minutes) and C (20 minutes). 783 mg of diphosphatidylchoxene (DPPC) (Avanti), 180 mg Cholesterol (Sigma), and 36mg Dicetyl-Phosphate (Sigma) was added to each of the flasks. 25 mg N-(1-pyrene sulfonyl)-1,2 hexadecanoyl-sn-glycero-3 phosphoethanolamine, triethylammonium sale (PS DHPE) (Molecular Probes Inc.) was then dissolved in 1 ml of chloroform and 320 ul (8 mg) was added into each of the round bottom flasks. Next, 2680 (3 ml–320 ul) of chloroform was added to each flask. Each flask was then placed in a rotovapor (Brinkman) with water bath set to 45° C. until dry. All available antigen was pooled into a 200 ml beaker in a hoop equipped with a Hepa filter and mixed well. 250 mg of maltose (Sigma) was measured into 3 50 ml centrifuge tubes. 50 ml of pooled antigen containing about $4 \times 10^5$ pfu of each virus was added to each tube and then one tube was added to flask C and warmed for 5 min in 50° C. water bath and then sonicated in a sonicator manufactured by Brinkman Inc. at a setting of 10,000 meters per second adjustable to 1–100,000 meters per second and at the same temperature for 20 minutes. The second tube of antigen/maltose mixture was added to flask B, warmed for 5 minutes in 50° C. water bath and sonicated for 5 minutes. The last tube of antigen/maltose was added to flask A, warmed for 5 minutes in 50° C. water bath and sonicated for 2 minutes. Aliquots of 1 ml were then removed for particle sizing. The remaining batches were placed in separate specimen cups labeled appropriately and placed at −70° C. until lyophilization.

Immunizations and Experimental Methods

The resultant 3 liposomes (2 um, 10 um, 908 nm) were given to male CD-1 mice weighing 16–18 g obtained from Charles Rivers Farms, Wilmington, Mass. orally either alone or mixed for either 1 2 or 3 doses over the same number of weeks. For all experiments, 30 mg liposomes were given orally in 0.3 cc containing sodium acetate buffer, pH 9.0. In one experiment, 120 mg of mixed liposomes were given. The final set of mice were given either mixed liposomes or a placebo and then infected with CVB5/C59.

The mice were then sacrificed. Blood samples, Peyer's patches and spleens were taken for microtiter neutralization antibody titration assays and Electron Microscopy work respectively. Pancreas samples were taken only from infected mice to run viral titer assays.

Neutralizing Antibody Titration Assay

For each mouse, a serum sample was taken, prepared, and assayed for antibody response as previously described in See, D. M., Tilles, J. G., "Efficacy of a Polyvalent Inactivated-virus Vaccine in Protecting Mice from infection with Clinical Strains of Group B Coxsackieviruses," Scand. J. Infect. Dis. 26:739–747, 1994. After serum and virus were incubated at room temperature for 1 hour, MK cells from one 75 cm² tissue flask were added directly to the microtiter plate.

Virus Assay

For each mouse, a pancreas sample was taken, homogenized in supplemented L15 diluent and assayed for virus by the plaque technique described previously in See, D. M., Tilles, J. G., "Treatment of Coxsackievirus A9 Myocarditis in Mice with WIN 54954," Antimicrob. Agents Chemother. 36:425–428, 1992, the disclosure of which is incorporated herein by reference, with the modification of using MK rather than Foreskin Fibroblast cells.

Electron Microscopy

Peyer's patches and spleens were diced into pieces <1 mm with a single edged blade on a wax sheet and kept moist in 0.1M phosphate buffer. The pieces were then added to a vial of gluteraldehyde solution prepared by mixing 0.2M phosphate buffer, pH 7 (28 ml 0.2M $NaH_2PO_4$+72 ml 0.2M $Na_2HPO_4$) 1:1 with 8% gluteraldehyde (Ted Pella Inc.). Tissue was fixed 2–4 hours at room temperature and then washed 3 times with 0.1M phosphate buffer. Samples were then taken to University of California Irvine Imaging Facility to process for the Electron Microscopy.

Results

Induction of Antibody

To show the success of the liposome vaccine in stimulating a specific antibody response in mice, serial determinations of neutralizing antibody to all six coxsackie serogroups were made in groups of 5 mice for each liposome tested. Means for each liposome were calculated for neutralizing antibody titer in plasma obtained 8–60 days after final dose of vaccine. Eight days after final dose of liposomes, a modest rise in titer to all strains tested was recorded. The smallest liposome (909 nm) gave the largest initial response after one dose (mean 4.2+/−SD2.3) but had little increase with repeated doses. The largest (10 um) liposome resulted in the greatest antibody response after 3 doses but did not result in detectable antibody levels 24 days after final dose. A single dose of the mixed liposomes produced an antibody response still detectable 21 days after final dose.

The results are shown in Table 1 below.

TABLE 1

Neutralizing antibody titers to 6 CVB strains after various doses of vaccine.

| Liposomes | # doses | Days since last dose | Mean Neutralizing Antibody Titer |
|---|---|---|---|
| 980 nm | 1 | 8 | 4.2+/−2.3 |
|  | 2 | 8 | 4.9+/−2.5 |
|  | 3 | 8 | 4.7+/−2.7 |
| 2 um | 1 | 8 | 3.3+/−1.8 |
|  | 2 | 8 | 4.7+/−2.9 |
|  | 3 | 8 | 6.2+/−3.6 |
| 10 um | 1 | 8 | 3.1+/−1.5 |
|  | 2 | 8 | 3.8+/−1.9 |
|  | 3 | 8 | 6.9+/−3.3 |
|  | 1 | 24 | <3 |
| Mixed | 1 | 8 | 3.9+/−1.7 |
|  | 2 | 8 | 4.9+/−2.5 |
|  | 3 | 8 | 7.6+/−2.9 |
|  | 1* | 24 | 4.8+/−2.7 |
|  | 3* | 24 | 8.8+/−3.3 |
|  | 1+ | 60 | 4.7+/−2.9 |

Notes: n = 5 for each group. Titers <3 were assigned a value of 2 for purposes of determining the mean. Means are for all 6 coxsackie B serogroups.
*30 mg
+120 mg Protection from Acute Infection with CVB5/C59 Viral Titer Assay To confirm the ability of the oral vaccination to limit challenge virus infection, titers of virus were determined in the pancreas of mice killed 3 days after infection. Two groups of 5 mice were used; one group was given 3 doses of mixed liposomes and the other group was given buffer placebo. The placebo group ended up with a mean titer of $5.3 \times 10^4$ (pfu/mg) while the vaccine group's mean titer was only $2.2 \times 10^2$ (pfu/mg). (Titers of <2 (the lower limit of sensitivity of the assay) were assigned a value of 1 for the purpose of calculating the mean.)

Electron Microscopy

Figure 13:
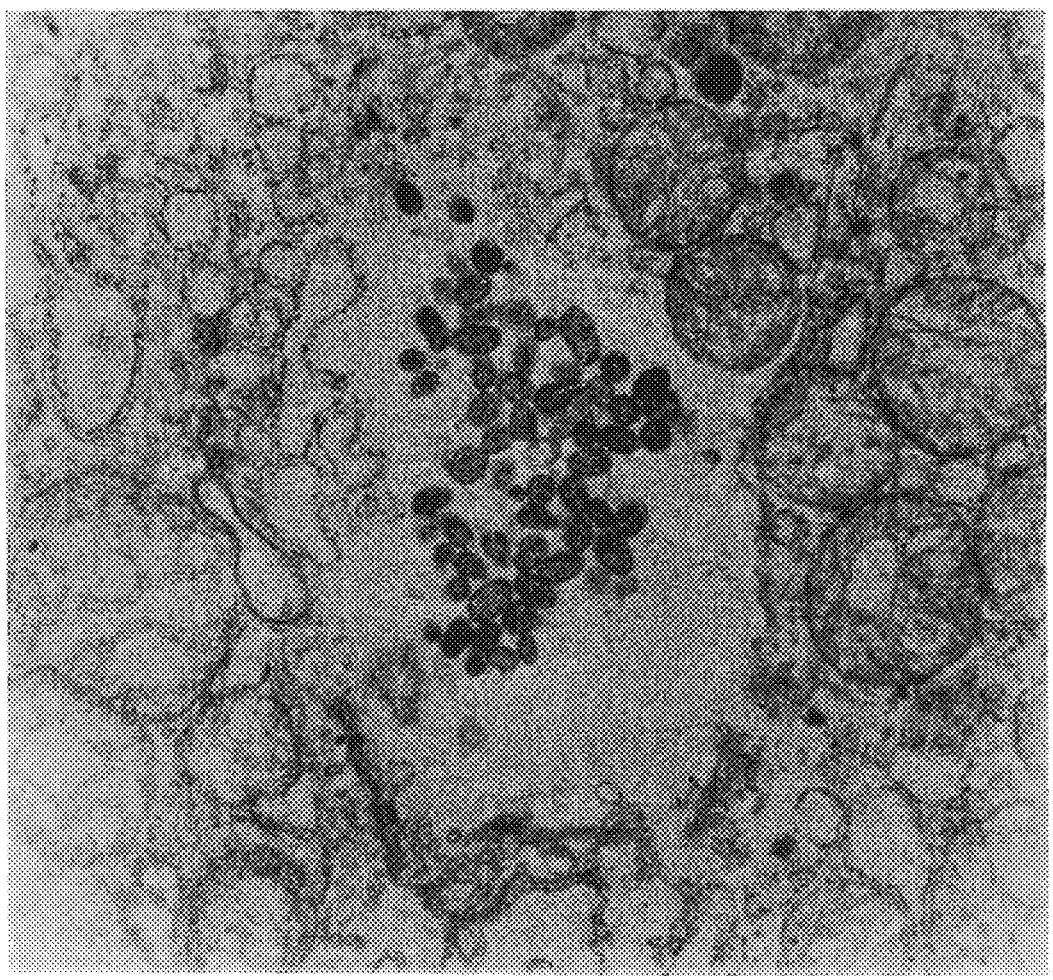
FIG. 13 is an electron photomicrograph (magnification 25,000×) showing 980 nm liposomes in a macrophage vacuole 7 days after oral inoculation.
Figure 14:
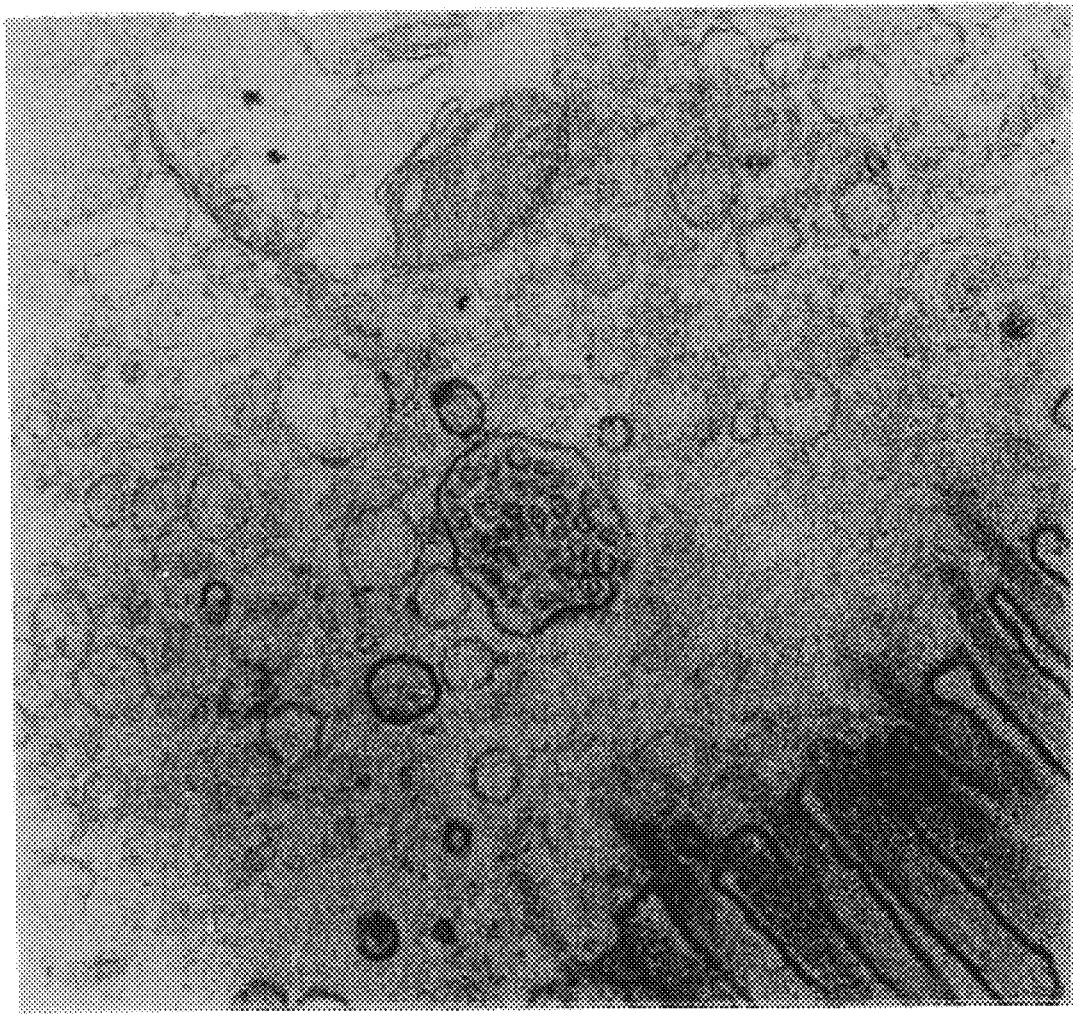
FIG. 14 is an electron photomicrograph (magnification 12,500×) showing 10 micron liposomes in a macrophage 21 days after oral inoculation.
Figure 15:
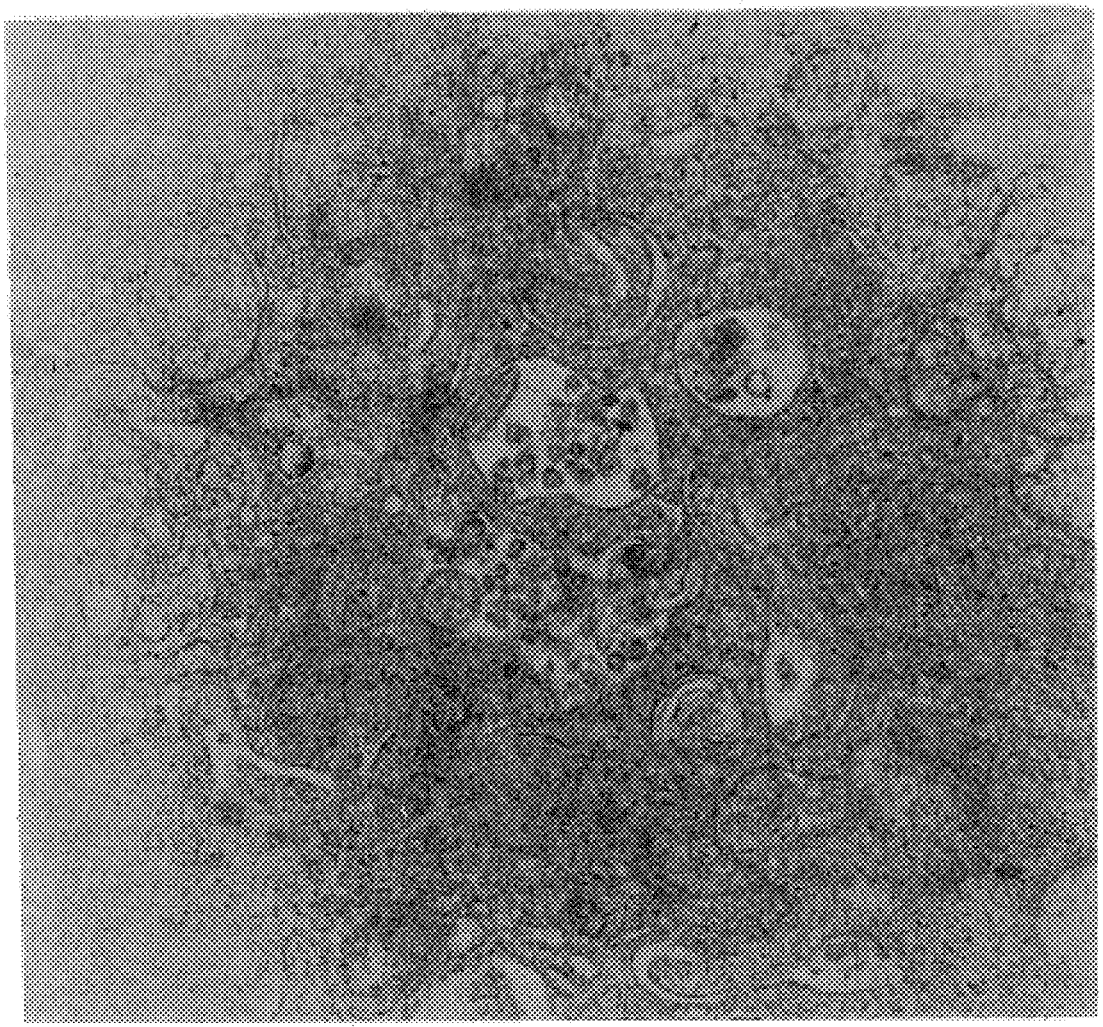
FIG. 15 is an electron photomicrograph (magnification 40,000×) showing 2 micron liposomes in a macrophage vacuole 60 days after oral inoculation.

As shown in FIG. 13, seven days after final oral inoculation, 980 nm liposomes are visible in vacuoles within macrophages of the Peyer's Patches. As shown in FIG. 14, 21 days after oral inoculation, a 10 micron liposome was observed in a macrophage of the Peyer's patches. As shown in FIG. 15, 60 days after oral inoculation, 2 micron liposomes were observed in a vacuole within a macrophage of the Peyer's Patches.

EXAMPLE 3

Antigen p24 antigen was purchased from Biodesign International, Kennebunk, Me.

Animals

Male CD-1 Mice 16–18 g were obtained from Charles Rivers Farms, Wilmington, Mass.

Microencapsulation p24 antigen was encapsulated in 3 different particle size liposomes as follows: A solution of PyS DHPE was prepared in a test tube by dissolving 25 mg of PyS DHPE in 1.0 ml, of chloroform. Lipid solution was then prepared in a separate test tube by combining 313 mg of DPPC, 72 mg of cholesterol, 14 mg of dicetylphosphate, 144 µL PyS DHPE solution, and 1.056 ml of chloroform, for a total volume of approximately 1.20 mL.

900 µL, of the lipid solution was aliquoted into a glass test tube. The solvent in each tube was evaporated to dryness with Nitrogen gas. A maltose solution was prepared by dissolving 100 mg of maltose in 1.0 mL of water. 750 μL of maltose solution was measured into the three test tubes. 200 μL of p24 antigen was added to each tube, then 4550 μL of water was added.

The solution in the first tube was warmed at 50° C. for 2 minutes then sonicated at 50° C. for 2 minutes to obtain liposomes have a diameter of approximately 5 μm. The solution in the second tube was warmed at 50° C. for 2 minutes then sonicated at 50° C. for 5 minutes to obtain liposomes having a diameter of approximately 2 μm. The solution in the third test tube was warmed at 50° C. for 2 minutes, giving liposomes having a size of approximately 5 μm. Approximately 10 μl of liposomes was removed from each test tube for particle sizing. The liposomes from all three test tubes were combined for a total volume of approximately 15 ml. The solution was aliquoted into glass vials (1.5 mL/vial; 60 μg/vial). The vials were placed in a −10° C. freezer overnight. The samples were then lyophilized.

Immunizations and Experimental Methods

The resultant lyophilized liposome mixtures of three different-sized liposomes (1 μm, 2 μm, and 5 μm) were orally administered to male CD-1 mice weighing 16–18 g obtained from Charles Rivers Farms, Wilmington, Mass. For all experiments, 30 mg liposome mixtures were orally administered in 0.3 cc containing sodium acetate buffer, pH 9.0, so that each mouse received 60 μg of p24 antigen. The mice were then sacrificed. Blood samples, Peyer's patches and spleens were taken for antibody to p24 antigen by Enzyme Immunolinked Assay (EIA), Electron Microscopy work, and lymphocyte proliferation assay, respectively.

Electron Microscopy

Peyer's patches and spleens were diced into pieces <1 mm with a single edged blade on a wax sheet and kept moist in 0.1M phosphate buffer. The pieces were then added to a vial of gluteraldehyde solution prepared by mixing 0.2M phosphate buffer, pH 7 (28 ml 0.2M $NaH_2PO_4$+72 ml 0.2M $Na_2HPO_4$) 1:1 with 8% gluteraldehyde (Ted Pella Inc.). Tissue was fixed 2–4 hours at room temperature and then washed 3 times with 0.1M phosphate buffer. Samples were then taken to University of California Irvine Imaging Facility to process for the Electron Microscopy.

Induction of Antibody

To show the success of the liposome vaccine in stimulating a specific antibody response in mice, EIA assays to p24 antigen were conducted at weekly intervals for 5 weeks. By the fifth week, both mice assayed had developed antibodies to the p24 antigen.

Lymphocyte Proliferation Assay

To determine the ability of liposomal p24 antigen to induce a cellular immune response, a lymphocyte proliferation assay was performed after week two and week four. Proliferation of splenic mononuclear cells was significantly enhanced in liposomal p24 antigen-treated mice compared to untreated control mice, as shown in Table 2 below. The proliferation index indicates the extent of cellular proliferation resulting from prior exposure to p24 antigen compared to a control not previously exposed to the antigen, and takes into account the amount of p24 antigen added to the assay. A higher proliferation index indicates more cellular proliferation and therefore a better cellular immune response. A proliferation index of at least 1 indicates a very active immune response.

TABLE 2

| Added Antigen | Proliferation Index |
| --- | --- |
| Week 2 | |
| 40 mcg | 4.95 |
| 80 mcg | 6.16 |
| 120 mcg | 5.58 |
| Week 4 | |
| 0.1 mcg | <1.0 |
| 1 mcg | 1.5 |
| 10 mcg | 4.3 |

Electron Microscopy

By the second week after vaccination, liposomes were seen in macrophages of the Peyer's patches.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise embodiments described and illustrated in the accompanying drawings, but rather should be read consistent with and as support to the following claims which are to have their fullest and fair scope.

What is claimed is:

1. A method for stimulating a systemic immune response to an antigen selected from the group consisting of inactivated HIV I and HIV II antigens and combinations thereof in a mammal comprising:

providing a lipsomal preparation comprising lyophilized liposomes containing at least one antigen selected from the group consisting of inactivated HIV I and HIV II antigens, wherein the liposomes have at least three different sizes and consist essentially of:

at least 5% by volume, based on the total volume of liposomes in the preparation, small liposomes having a size, before lyophilization, of from about 20 nm to about 1 micron, at least 5% by volume, based on the total volume of liposomes in the preparation, medium liposomes having a size, before lyophilization, of from about 1 micron to about 3 microns, and at least 5% by volume, based on the total volume of liposomes in the preparation, large liposomes having a size, before lyophilization, of from about 3 microns to about 20 microns; and orally administering an effective amount of the liposomal preparation to a mammal, whereby sufficient antigen containing liposomes are absorbed in the Peyer's patches of the gut of the mammal and are taken up by macrophages in the Peyer's patches to stimulate a systemic immune response.

2. A method as claimed in claim 1, wherein the liposomes are multi-lamellar before lyophilization.

3. A method as claimed in claim 1, wherein the liposomal preparation is contained within an enterically-coated capsule.

4. A method as claimed in claim 1 wherein the liposomes consist essentially of at least 5% by volume, based on the total volume of liposomes in the preparation, small liposomes having a size, before lyophilization, of from about 20 nm to about 1 micron, at least 10% by volume, based on the total volume of liposomes in the preparation, medium liposomes having a size, before lyophilization, of from about 1 micron to about 3 microns, and at least 20% by volume, based on the total volume of liposomes in the preparation, large liposomes having a size, before lyphilization, of from about 3 microns to about 20 microns.

5. A method as claimed in claim 1 wherein the liposomes comprise about 10% by volume, based on the total volume of liposomes in the preparation, small liposomes having a size, before lyophilization, of from about 20 nm to about 1 micron, about 25% by volume, based on the total volume of liposomes in the preparation, medium liposomes having a size, before lyophilization, of from about 1 micron to about 3 microns, and about 65% by volume, based on the total volume of liposomes in the preparation, large liposomes having a size, before lyopilization, of from about 3 microns to about 20 microns.

6. A method as claimed in claim 1 wherein the liposomes comprise at least two different antigens.

7. A preparation for oral administration to a mammal capable of stimulating a systemic immune response to at least one antigen selected from the group consisting of inactivated HIV I and HIV II antigens, said preparation comprising an effective amount of lyophilized antigen-containing liposomes, wherein the liposomes have at least three different sizes, before lyophilization, and consist essentially of:
   at least 5% by volume, based on the total volume of liposomes in the preparation, small liposomes having a size, before lyophilization, of from about 20 nm to about 1 micron,
   at least 5% by volume, based on the total volume of liposomes in the preparation, medium liposomes having a size, before lyophilization, of from about 1 micron to about 3 microns, and
   at least 5% by volume, based on the total volume of liposomes in the preparation, large liposomes having a size, before lyphilization, of from about 3 microns to about 20 microns.

8. A preparation as claimed in claim 7 wherein the liposomes are multi-lamellar before lyophilization.

9. A preparation as claimed in claim 7 wherein the liposome preparation is contained within an enterically-coated capsule.

10. A preparation as claimed in claim 7 wherein the liposomes comprise small, medium and large liposomes.

11. A preparation as claimed in claim 7 wherein the liposomes consist essentially of at least 5% by volume, based on the total volume of liposomes in the preparation, small liposomes having a size, before lyophilization, of from about 20 nm to about 1 micron, at least 10% by volume, based on the total of liposomes in the preparation, medium liposomes having a size, before lyophilization, of from about 1 micron to about 3 microns, and at least 20% by volume, based on the total volume of liposomes in the preparation, large liposomes having a size, before lyophilization, of from about 3 microns to about 20 microns.

12. A preparation as claimed in claim 7 wherein the liposomes consist essentially of about 10% by volume, based on the total volume of liposomes in the prepartion, small liposomes having a size, before lyophilization, of from about 20 nm to about 1 micron, about 25% by volume, based on the total volume of liposomes in the preparation, medium liposomes having a size, before lyophilization, of from about 1 micron to about 3 microns, and about 65% by volume, based on the total volume of liposomes in the preparation, large liposomes having a size, before lyophilization, of from about 3 microns to about 20 microns.

13. A preparation as claimed in claim 7 wherein the liposomes comprise at least two different antigens.

14. A method according to claim 1, wherein the large liposomes have a size, before lyophilization, of from about 3 microns to about 10 microns.

15. A method according to claim 1, wherein the large liposomes have a size, before lyophilization, of from about 3 microns to about 5 microns.

16. A method according to claim 1, wherein the small liposomes have a size, before lyophilization, of about 1 micron.

17. A method according to claim 1, wherein the medium liposomes have a size, before lyophilization, of about 2 microns.

18. A method according to claim 1, wherein the large liposomes have a size, before lyophilization, of about 10 microns.

19. A method according to claim 1, wherein the small liposomes have a size, before lyophilization, of about 1 micron, the medium liposomes have a size, before lyophilization, of about 2 microns, and the large liposomes have a size, before lyophilization, of about 10 microns.

20. A method according to claim 4, wherein the large liposomes have a size, before lyophilization, of from about 3 microns to about 10 microns.

21. A method according to claim 4 wherein the large liposomes have a size, before lyophilization, of from about 3 microns to about 5 microns.

22. A method according to claim 4, wherein the small liposomes have a size, before lyophilization, of about 1 micron.

23. A method according to claim 4, wherein the medium liposomes have a size, before lyophilization, of about 2 microns.

24. A method according to claim 4, wherein the large liposomes have a size, before lyophilization, of about 10 microns.

25. A method according to claim 4, wherein the small liposomes have a size, before lyophilization, of about 1 micron, the medium liposomes have a size, before lyophilization, of about 2 microns, and the large liposomes have a size, before lyophilization, of about 10 microns.

26. A method according to claim 5, wherein the large liposomes have a size, before lyophilization, of from about 3 microns to about 10 microns.

27. A method according to claim 5, wherein the large liposomes have a size, before lyphilization, of from about 3 microns to about 5 microns.

28. A method according to claim 5, wherein the small liposomes have a size, before liphilization, of about 1 micron.

29. A method according to claim 5, wherein the medium liposomes have a size, before lyophilization, of about 2 microns.

30. A method according to claim 5, wherein the large liposomes have a size, before lyophilization, of about 10 microns.

31. A method according to claim 5, wherein the small liposomes have a size, before lyophilization, of about 1 micron, the medium liposomes have a size, before lyophilization, of about 2 microns, and the large liposomes have a size, before lyophilization, of about 10 microns.

32. A prepairation according to claim 7, wherein the large liposomes have a size, before lyophilization, of from about 3 microns to about 10 microns.

33. A preparation according to claim 7, wherein the large liposomes have a size, before lyophilization, of from about 3 microns to about 5 microns.

34. A preparation according to claim 7, wherein the small liposomes have a size, before lyophilization, of about 1 micron.

35. A preparation according to claim 7, wherein the medium liposomes have a size, before lyophilization, of about 2 microns.

36. A preparation according to claim 7, wherein the large liposomes have a size, before lyophilization, of about 10 microns.

37. A preparation according to claim 7, wherein the small liposomes have a size, before lyophilization, of about 1 micron, the medium liposomes have a size, before lyophilization, of about 2 microns and the large liposomes have a sizes before lyophilization, of about 10 microns.

38. A preparation according to claim 11, wherein the large liposomes have a size, before lyophilization, of from about 3 microns to about 10 microns.

39. A preparation according to claim 11, wherein the large liposomes have a size, before lyophilization, of from about 3 microns to about 5 microns.

40. A preparation according to claim 11, wherein the small liposomes have a size, before lyophilization, of about 1 micron.

41. A preparation according to claim 11, wherein the medium liposomes have a size, before lyophilization, of about 2 microns.

42. A preparation according to claim 11, wherein the large liposomes have a size, before lyophilization, of about 10 microns.

43. A preparation according to claim 11, wherein the small liposomes have a size, before lyophilization, of about 1 micron, the medium liposomes have a size, before lyophilization, of about 2 microns, and the large liposomes have a size, before lyophilization, of about 10 microns.

44. A preparation according to claim 12, wherein the large liposomes have a size, before lyophilization, of from about 3 microns to about 10 microns.

45. A preparation according to claim 12, wherein the large liposomes have a size, before lyophilization, of from about 3 microns to about 5 microns.

46. A preparation according to claim 12, wherein the small liposomes have a size, before lyophilization, of about 1 micron.

47. A preparation according to claim 12, wherein the medium liposomes have a size, before lyophilization, of about 2 microns.

48. A preparation according to claim 12, wherein the large liposomes have a size, before lyophilization, of about 10 microns.

49. A preparation according to claim 12, wherein the small liposomes have a size, before lyophilization, of about 1 micron, the medium liposomes have a size, before lyophilization, of about 2 microns, and the large liposomes have a size, before lyophilization, of about 10 microns.

50. A method according to claim 1 wherein the antigen containing liposomes are capable of being absorbed in the Peyer's patches of the gut of the mammal and are capable of being taken up by macrophages in the Peyer's patches to stimulate a systemic immune response without the presence of an adjuvant.

51. A method according to claim 1 wherein the antigen containing liposomes are capable of being absorbed in the Peyer's patches of the gut of the mammal and are capable of being taken up by macrophages in the Peyer's patches to stimulate a systemic immune response without generating a typical adjuvant effect.

* * * * *

UNITED STATES PATENT AND TRADEMARK OFFICE
CERTIFICATE OF CORRECTION

PATENT NO.     : 6,207,185 B1
DATED          : March 27, 2001
INVENTOR(S)    : Jackie R. See and Darryl M. See It is certified that error appears in the above-identified patent and that said Letters Patent is hereby corrected as shown below:

<u>Title page,</u>
Item [56], References Cited, OTHER PUBLICATIONS, in "Chen, H. et al." replace ". . . oral vaccine carriess. . ." with -- . . . oral vaccine carriers. . . --.

<u>Column 15,</u>
Line 6, replace "lyphilization" with -- lyophilization --.
Line 17, replace "lyopilization" with -- lyophilization --.
Line 39, replace "lyphilization" with -- lyophilization --.
Line 53, after "total" insert -- volume --.
Line 61, replace "prepartion" with -- preparation --.

<u>Column 16,</u>
Line 49, replace "lyphilization" with -- lyophilization --.
Line 53, replace "liphilization" with -- lyophilization --.
Line 65, replace "prepairation" with -- preparation --.

<u>Column 17,</u>
Line 17, replace "sizes" with -- size, --.

Signed and Sealed this

Fourth Day of June, 2002

Attest:

JAMES E. ROGAN
Director of the United States Patent and Trademark Office

*Attesting Officer*